United States Patent [19]

Abraham

[11] Patent Number: 5,648,375
[45] Date of Patent: Jul. 15, 1997

[54] USE OF HYDROPHOBIC COMPOUNDS AND ANESTHETICS IN COMBINATION WITH ALLOSTERIC HEMOGLOBIN MODIFIERS

[75] Inventor: Donald J. Abraham, Midlothian, Va.

[73] Assignee: Virginia Commonwealth University, Richmond, Va.

[21] Appl. No.: 478,372

[22] Filed: Jun. 7, 1995

Related U.S. Application Data

[63] Continuation-in-part of Ser. No. 374,206, Jan. 18, 1995, and Ser. No. 101,501, Jul. 30, 1993, Pat. No. 5,432,191, which is a continuation-in-part of Ser. No. 6,246, Jan. 19, 1993, Pat. No. 5,290,803, which is a continuation-in-part of Ser. No. 702,947, May 20, 1991, Pat. No. 5,122,539, which is a continuation-in-part of Ser. No. 478,848, Feb. 22, 1990, Pat. No. 5,049,695.

[51] Int. Cl.$^6$ .............. A61K 31/40; A61K 31/325; C07C 45/00
[52] U.S. Cl. .............. 514/421; 514/486; 514/512; 514/513; 514/533; 514/535; 514/538; 514/833; 560/30; 560/31; 560/32; 562/452; 562/455; 562/425; 548/403; 548/416; 548/473; 548/478; 568/452

[58] Field of Search .............. 514/421, 486, 514/512, 513, 533, 535, 538, 833; 560/30, 31, 32; 562/425, 452, 455; 548/403, 416, 473, 478; 568/452

[56] References Cited

U.S. PATENT DOCUMENTS

| | | | |
|---|---|---|---|
| 4,921,997 | 5/1990 | Lalezari et al. | 560/34 |
| 5,122,539 | 6/1992 | Abraham et al. | 514/563 |
| 5,290,803 | 3/1994 | Abraham et al. | 514/421 |
| 5,382,680 | 1/1995 | Abraham et al. | 562/451 |
| 5,432,191 | 7/1995 | Abraham et al. | 514/421 |
| 5,525,630 | 6/1996 | Hoffman | 514/563 |

*Primary Examiner*—Porfirio Nazario-Gonzalez
*Attorney, Agent, or Firm*—Whitham, Curtis, Whitham & McGinn

[57] ABSTRACT

Allosteric hemoglobin modifier compound activity on p50 is potentiated by using the compound in combination with a hydrophobic compound such as an anesthetic.

7 Claims, 2 Drawing Sheets

USE OF HYDROPHOBIC COMPOUNDS AND ANESTHETICS IN COMBINATION WITH ALLOSTERIC HEMOGLOBIN MODIFIERS

CROSS-REFERENCE TO RELATED APPLICATIONS

This patent application is a continuation-in-part (CIP) application of the application filed Jan. 18, 1995, having U.S. Ser. No. 08/374,206, pending, and is a CIP application of the application filed Jul. 30, 1993, having U.S. Ser. No. 08/101,501, now U.S. Pat. No. 5,432,191 which itself is a CIP of the application filed Jan. 19, 1993, having U.S. Ser. No. 08/006,246, now U.S. Pat. No. 5,290,803, which was a CIP of the application filed May 20, 1991, having U.S. Ser. No. 07/702,947, now U.S. Pat. No. 5,122,539, which was a CIP of the application filed Feb. 22, 1990, having U.S. Ser. No. 07/478,848, now U.S. Pat. No. 5,049,695. The complete contents of each of these patent applications and patents are herein incorporated by reference.

DESCRIPTION

BACKGROUND OF THE INVENTION

1. Field of the Invention

The invention is generally related to the use of a combination of allosteric hemoglobin modifier compounds and hydrophobic compounds to allosterically modify hemoglobin towards a low oxygen affinity state. More particularly, the invention utilizes hydrophobic compounds, such as anesthetics, to enhance the efficacy of the hydrophobic compounds.

2. Description of the Prior Art

Allosteric hemoglobin modifier compounds are compounds that affect how tightly the hemoglobin molecule in blood holds oxygen molecules. Varying the degree to which oxygen is held to hemoglobin can have profound effects on a wide variety of blood disorders. For example, certain allosteric hemoglobin modifier compounds may cause oxygen to be held relatively more tightly than in the absence of the compound, and this may be useful in the treatment of disorders such as sickle cell anemia, while other compounds may cause oxygen to be held less tightly, thus causing blood to off-load oxygen more easily, and this may be useful in the treatment of disorders such as hypoxia.

SUMMARY OF THE INVENTION

It is an object of this invention to provide an improved method of treating a patient with allosteric hemoglobin modifier compounds.

It is another object of this invention to provide a pharmaceutical combination which includes a hydrophobic compound, such as an anesthetic, and an allosteric hemoglobin modifier compound.

It is yet another object of this invention to increase the p50 of hemoglobin in whole blood in a patient which can be achieved with allosteric hemoglobin modifier compounds and to increase the duration of the effect of the allosteric hemoglobin modifier compounds on p50 by administering the allosteric hemoglobin modifier compounds in combination with anesthesia or other hydrophobic compounds.

According to the invention, the efficacy of allosteric hemoglobin modifier compounds is enhanced in vivo when combined with hydrophobic compounds such as anesthetics. Thus, the desired allosteric results can be achieved with lower dosages of the allosteric hemoglobin modifier compounds and/or the allosteric hemoglobin modifier compounds can be used to achieve more rapid and superior results when used in combination with the hydrophobic compounds. Experiments with animals have shown that there is an increase in p50 due to allosteric hemoglobin modifier compounds when they are used in the presence of hydrophobic compounds such as anesthesia and that the duration of the effect on p50 is increased when the allosteric effector compounds are used in the presence of hydrophobic compounds.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
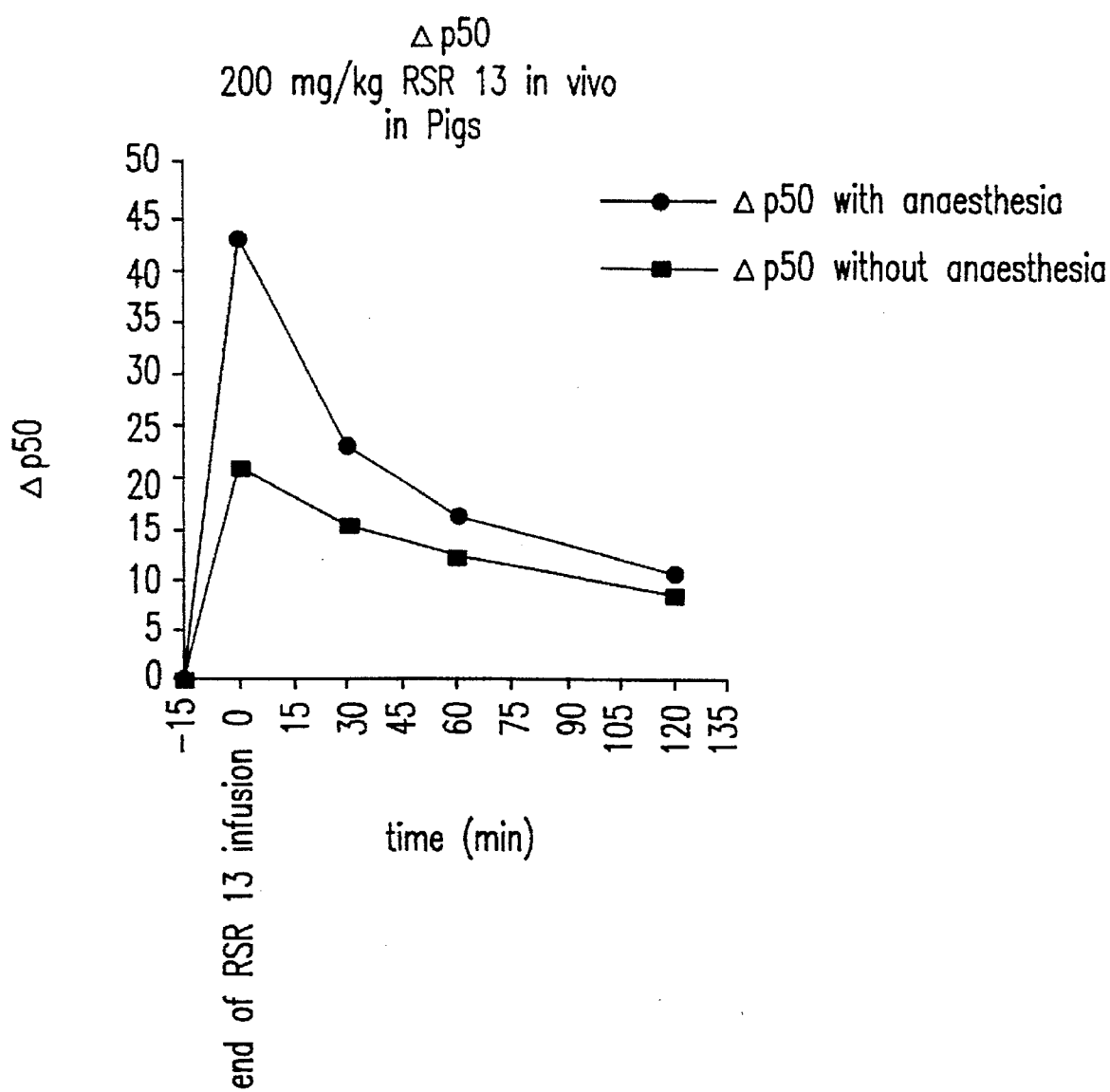
FIG. 1 is a graph comparing the $\Delta$p50 versus time results for pigs treated with anesthesia in combination with RSR 13, and pigs treated with RSR 13 alone.

Allosteric hemoglobin modifier compounds are well known in the field. These compounds interact with the hemoglobin molecule and impact on hemoglobin-oxygen binding. This invention is particularly concerned with allosteric hemoglobin modifier compounds that cause oxygen to be bound relatively less tightly to hemoglobin, such that oxygen is off-loaded from the hemoglobin molecule more easily. Examples of some allosteric hemoglobin modifier compounds which can be used within the practice of this invention are discussed in detail in the patents and patent applications identified above which have been incorporated by reference. These compounds have the structural formula:

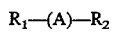

where $R_1$ and $R_2$ each are a substituted or unsubstituted aromatic or heteroaromatic compound, or a substituted or unsubstituted alkyl or heteroalkyl ring compound, or a substituted or unsubstituted phthalimide compound, and where $R_1$ and $R_2$ may be the same or different, where A is a chemical bridge which includes 2–4 chemical moieties bonded together between $R_1$ and $R_2$, wherein said chemical moieties in A are selected from the group consisting of CO, O, S, $SO_2$, NH, $NR_3$ where $R_3$ is a $C_{1-6}$ alkyl group, $NR_4$ where $R_4$ includes two carbonyls as part of a phthalimide compound formed with $R_1$ or $R_2$, $CH_2$, CH, and C, and where at least one of $R_1$ and $R_2$ is substituted with a compound having the chemical formula:

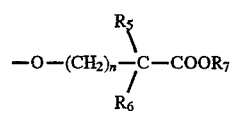

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moities may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group. A particularly preferred allosteric hemoglobin modifier compound useful in the practice of this invention is identified as "RSR-13" and has the chemical formula: 2-[4-((((3,5-dimethylphenyl)amino)carbonyl) methyl)phenoxy]-2-methyl propionic acid.

Wilson and Gisvold's Textbook of Organic Medicinal and Pharmaceutical Chemistry, Eighth Edition (1982), shows that a neuromuscular blocking agent (mylaxen) is relatively ineffective unless a hydrophobic lipophilic anesthetic is used in combination with the blocking agent. The anesthetic saturates the body's neutral fat depots and lipophilic receptor sites. When the sites are blocked by the anesthetics, the neuromuscular blocking agent increases in concentration at the desired active site and is made potent. When the anesthetic is not present, the neutral fat depots and lipophilic receptors bind the neuromuscular blocking agent and lower its concentrate on at the desired site of action, thereby lowering its potency.

It has been determined that allosteric hemoglobin modifier compounds are hydrophobic molecules that can, like the neuromuscular agent discussed above, be bound to the the body's neutral fat depots and lipophilic receptors sites, thus lowering its potency due to a decreased concentration in the red cell where hemoglobin is bound. Administration of a hydrophobic compound, such as the mixture of anesthetic molecules discussed below, will saturate the body's neutral fat depots and lipophilic receptor sites and thereby increase the concentration of allosteric modifiers in the red cell where higher concentrations of effector will increase its ability to interact with hemoglobin and deliver more oxygen.

Experiments were conducted to determine if the use of hydrophobic compounds, such as anesthetics, would have any benefit on increasing effector action. The experiments were conducted in vivo in Male Yorkshire pigs weighing approximately 16–21 kg.

In the experiments, one group of "control" pigs were administered, via intravenous infusion over the course of 15 minutes, 200 mg/kg 2-[4-((((3,5-dimethylphenyl)amino) carbonyl) methyl)phenoxy]-2-methyl propionic acid (RSR 13) in 0.45% saline vehicle, and another group of "anesthetized" pigs were administered the same 200 mg/kg dose of RSR 13, however, the "anesthetized" pigs were also administered fentanyl (3–10 µg/kg) and thiopental (20 mg/kg) to induce anesthesia at the time of RSR 13 administration to induce anesthesia. The "anesthetized" pigs were ventilated with 20–50% nitrous oxide in oxygen and 0.25% isoflurane during the course of the study to maintaine a stable plane of deep anesthesia. In both groups, infusion of 0.45% vehicle alone preceeded infusion of RSR-13. One ml samples of venous blood were withdrawn from the pigs in both groups prior to infusion of the saline vehicle, prior to infusion of RSR-13, immediately prior to termination of RSR-13 infusion, and at the following times after termination of the RSR-13 infusion: 30 min., 60 min., 120 min., and 180 min. The samples were drawn into a 1-ml syringe containing 0.05 ml. of sodium heparin (1000 USP units/ml). These samples were used to measure, with an oxygen electrode, the partial pressure of oxygen ($pO_2$), and, with a carbon dioxide electrode, the partial pressure of carbon dioxide ($pCO_2$). The pH was also measured. In one study, the measured values were used to estimate oxygen saturation and p50, which is the partial pressure of oxygen when hemoglobin is 50% saturated with oxygen.

In estimating p50 values, the $PO_2$ values obtained from the venous blood samples were initially corrected for pH using the procedure described in Severinhaus, *J. Appl. Phys.* 46:599 (1979). The values of corrected $pO_2$ and oxygen saturation were then superimposed on a standard human oxygen dissociation curve, and the p50 value determined by extrapolation. This method relies on the basic similarity of mammalian oxygen dissociation curves. A correction factor of 4.2 was employed to adjust for the reported difference in basal p50 between humans and pigs, i.e., 26.6 mmHg for humans and 30.8 mmHg for pigs (see, FASEB Handbook of Respiration and Circulation, Altman P L, Dittmer D S, eds., Bethesda, Md. 1971, p. 139).

Table 1 presents the average estimated p50 for both the "control" and the "anesthetized" groups of pigs at various time points in the experiment.

TABLE 1

| Condition/Time of Measurement | Control Estimated p50 mmHg | Anesthetized Estimated p50 mmHg |
|---|---|---|
| (1) Basal | 31 | 33 |
| (2) Infusion of Vehicle | | |
| 15 min | 29 | 33 |
| (3) Infusion of RSR-13 | | |
| 15 min | 41 | 59 |
| (4) Post-Infusion of RSR-13 | | |
| 30 min | 42 | 49 |
| 60 min | 41 | 49 |
| 120 min | 37 | 49 |
| 180 min | 35 | 47 |

Table 1 clearly shows that there is both an increase in p50 due to the presence of anesthesia, and an increase in the duration of the allosteric activity indicated by the p50. Thus, the allosteric effector compounds of the present invention can best be administered in combination with hydrophobic and anesthetic compounds to have increased activity. The compounds can be administered by intravenous infusion or other means. The preferred dose of the allosteric effector compound is approximately 25–250 mg/kg body weight.

The change in p50 ($\Delta$p50) between pigs treated with RSR 13 alone and with the combination of anesthetic agents and RSR 13 was also measured directly using an Aminco Hem-O-Scan. The results are shown in FIG. 1. The graph indicates that anesthesia increases the effect of RSR 13 by more than double by the end of infusion of RSR 13. With anesthesia, the p50 remains elevated at 2 hrs post infusion of RSR 13.

Figure 2:
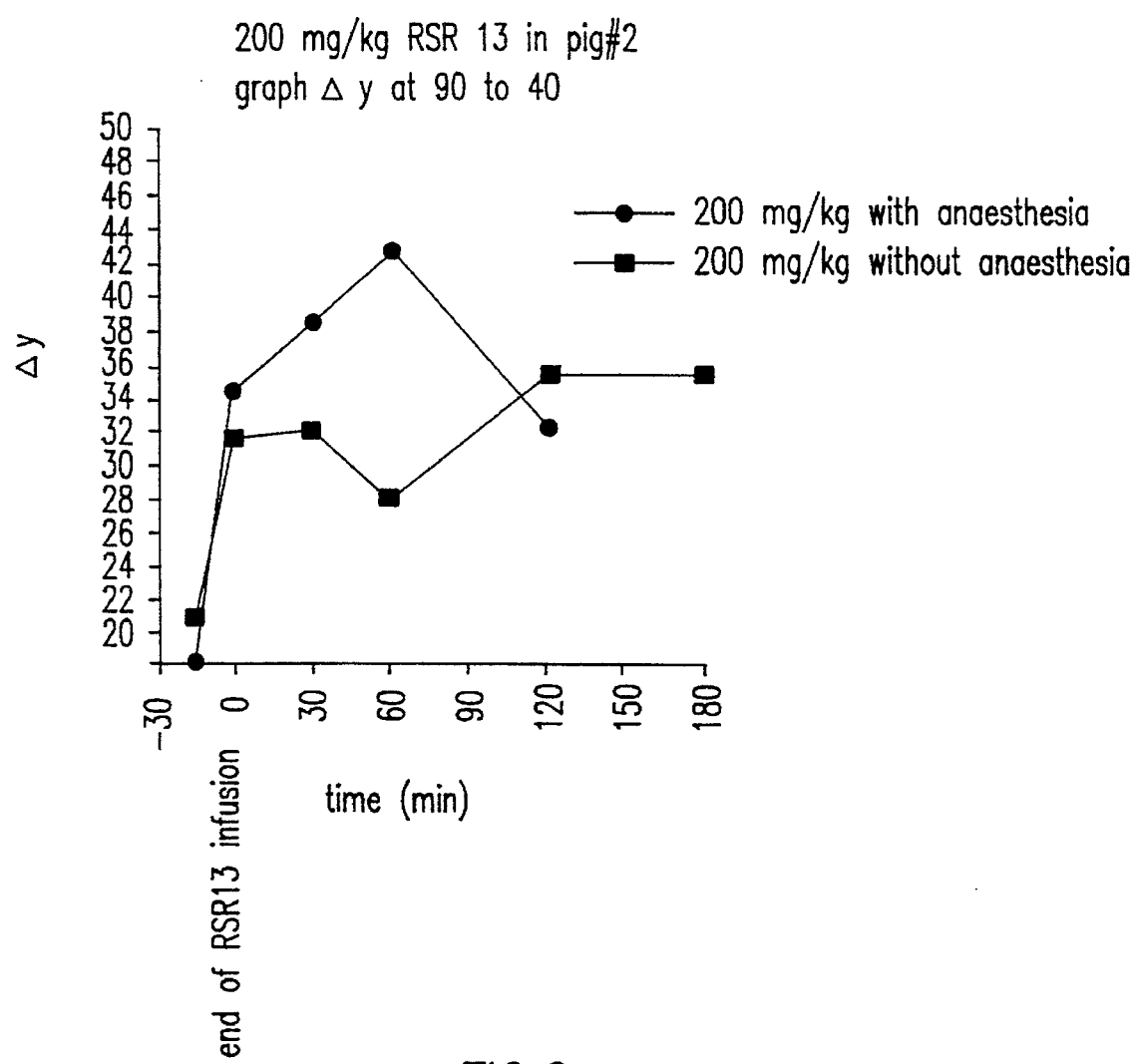
FIG. 2 is a graph comparing the $\Delta y$ versus time results for pigs treated with anesthesia in combination with RSR 13, and pigs treated with RSR 13 alone.

The larger amount of oxygen delivery in the presence of RSR 13 and anesthesia is shown in FIG. 2. The $\Delta y$ is the difference in the % oxygen between lung pressures of oxygen ($PO_2$=90 mm Hg) and cappilary pressures of oxygent ($PO_2$=40 mm Hg) calculated using the Hem-O-Scan curves. At 30 minutes after infusion, the figure clearly shows 6% more oxygen is delivered in the presence of anesthesia, and even greater amounts are delivered after 60 minutes (approximately 12%). These results clearly indicate that more oxygen can be delivered under physiological conditions to hypoxic tissues, organs, etc., in when the allosteric hemoglobin modifier compound is combined with a hydrophobic compound such as an anesthetic.

While anesthetic compounds were used in combination with allosteric effector compounds, other hydrophobic compounds could also be used to saturate the body's neutral fat depots and lipophilic receptor sites. The types of hydrophobic compounds which could be used in the practice of this invention include barbituates, such as thiopental; parentoral nutrition, such as interlipid; short chain fatty acids, such as butyric acid and phenyl butyrate; volatile anesthetics, such as cyclopropane halothane, ether, vinyl ether, enflurane, methoxyflurane, and penthrane; parentral general anesthetics such as propofol; anticonvulsives such as dilantin; and benzodiazapines. The does of the hydrophobic compound will depend on the compound and will be on the order of 1 µg/kg body weight to 1 g/kg body weight. Combinations of hydrophobic compounds can also be used. The hydrophobic compound(s) can be combined with the allosteric effector compound and administered simultaneously therewith, or can be supplied separately. Administration can be by intravenous infusion, oral delivery, or other means. Best results are obtained when the hydrophobic compound and allosteric effector compound are administered at approximately the same time.

While the invention has been described in terms of its preferred embodiments, those skilled in the art will recognize that the invention can be practiced with modification within the spirit and scope of the appended claims.

We claim:

1. A method of allosterically modifying hemoglobin in a patient towards a low oxygen binding states and increasing the delivery of oxygen to said patient, comprising the steps of:

administering an allosteric hemoglobin modifier compound to a patient, wherein said allosteric hemoglobin modifier compound has the structural formula:

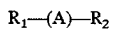

where $R_1$ and $R_2$ each are a substituted or unsubstituted aromatic or heteroaromatic compounds, or a substituted or unsubstituted alkyl or heteroalkyl ring compound, or a substituted or unsubstituted phthalimide compound, and where $R_1$ and $R_2$ may be the same or different, where A is a chemical bridge which includes 3 chemical moieties bonded together between $R_1$ and $R_2$, wherein said chemical moieties in A are selected from the group consisting of CO, O, S, $SO_2$, NH, $NR_3$ where $R_3$ is $C_{1-6}$ alkyl group, $NR_4$ where $R_4$ includes two carbonyls as part of a phthalimide compound formed with $R_1$ or $R_2$, $CH_2$, CH, and C, and where at least one of $R_1$ and $R_2$ is substituted with a compounds having the chemical formula:

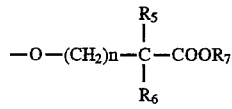

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group; and administering a hydrophobic compound to said patient, said two administering steps being performed at approximately the same time.

2. The method of claim 1 wherein said allosteric hemoglobin modifier compound is 2-[4-((((3,5-dimethylphenyl)amino) carbonyl)methyl)phenoxy]-2-methyl propionic acid.

3. The method of claim 1 wherein said hydrophobic compounds is selected from the group consisting of barbituates, parenteral nutrition, short chain fatty acids, volatile anesthetics, parenteral general anesthetics, anticonvulsives, and benzodiazapines.

4. The method of claim 3 wherein said hydrophobic compound is a volatile anesthetic.

5. A composition for allosterically modifying hemoglobin, comprising:

an allosteric hemoglobin modifier compound having the structural formula:

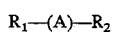

where $R_1$ and $R_2$ each are a substituted or unsubstituted aromatic or heteroaromatic compounds, or a substituted or unsubstituted alkyl or heteroalkyl ring compound, or a substituted or unsubstituted phthalimide compound, and where $R_1$ and $R_2$ may be the same or different, where A is a chemical bridge which includes 3 chemical moieties bonded together between R1 and R2, wherein said chemical moieties in A are selected from the group consisting of CO, O, S, $SO_2$, NH, $NR_3$ where $R_3$ is $C_{1-6}$ alkyl group, $NR_4$ where $R_4$ includes two carbonyls as part of a phthalimide compound formed with $R_1$ or $R_2$, $CH_2$, CH, and C, and where at least one of $R_1$ and $R_2$ is substituted with a compounds having the chemical formula:

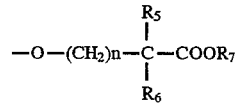

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group; and a hydrophobic compound.

6. The composition of claim 5 wherein said allosteric hemoglobin modifier compound is a 2-[4-((((3,5-dimethylphenyl)amino)carbonyl)methyl)phenoxy]-2-methyl propionic acid.

7. The composition of claim 5 wherein said hydrophobic compound is selected from the group consisting of barbituates, parenteral nutrition, short chain fatty acids, volatile anesthetics, parenteral general anesthetics, anticonvulsives, and benzodiazapines.

* * * * *